United States Patent [19]

Muenster et al.

[11] Patent Number: 5,538,939
[45] Date of Patent: Jul. 23, 1996

[54] ACYLAMINO-SUBSTITUTED ISOXAZOLE OR ISOTHIAZOLE DERIVATIVES, THEIR PREPARATION AND THEIR USE

[75] Inventors: Peter Muenster, Neulussheim; Ernst Schefczik, Ludwigshafen; Hartmann Koenig; Matthias Gerber, both of Limburgerhof; Karl-Otto Westphalen, Speyer; Helmut Walter, Obrigheim, all of Germany

[73] Assignee: BASF Aktiengesellschaft, Ludwigshafen, Germany

[21] Appl. No.: 293,959

[22] Filed: Aug. 24, 1994

[30] Foreign Application Priority Data

Aug. 24, 1993 [DE] Germany ............... 43 28 425.6

[51] Int. Cl.$^6$ .................. A01N 43/80; C07D 277/56; C07D 277/54; C07D 277/46
[52] U.S. Cl. ........................... 504/269; 548/214
[58] Field of Search ............ 548/214; 514/372; 504/269

[56] References Cited

U.S. PATENT DOCUMENTS

| 3,770,740 | 11/1973 | Burch | 260/256.4 |
| 4,032,321 | 6/1977 | Gibbons | 71/90 |
| 4,057,416 | 11/1977 | Gibbons | 71/90 |
| 4,059,433 | 11/1977 | Gibbons | 71/90 |

FOREIGN PATENT DOCUMENTS

| 105548 | 4/1984 | European Pat. Off. . |
| 1924830 | 5/1969 | Germany . |
| 2434922 | 7/1974 | Germany . |
| 59-128306 | 1/1983 | Japan . |

OTHER PUBLICATIONS

English abstract of JP-59 128 306A; Abstract No. 84-217100/35, (1983).
Goerdeler et al.; Chem. Ber., vol. 96, 1963, pp. 526–533.
Vicentini et al.; Pestic. Sci.; vol. 34, 1992, pp. 127–131.
Burch et al., J. of Med. Chem., vol. 17, No. 4, 1974, pp. 451–453.
Chem. Abst., vol. 80, 1974, Abs. No. 128066.
Desimoni et al., Tetrahedron, 1967, vol. 23, pp. 687–691.
Chem. Abst., vol. 74, 1971, Abs. No. 87882.
Machon et al., Archiv. Immunol. Ther. Exp., 21, 883–9 (1973).

Primary Examiner—Johann Richter
Assistant Examiner—Laura R. Cross
Attorney, Agent, or Firm—Keil & Weinkauf

[57] ABSTRACT

Acylamino-substituted isoxazole or isothiazole derivatives of the formula I

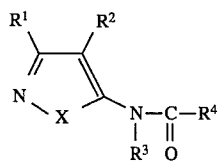

where X is oxygen or sulfur;

$R^1$ is unsubstituted or substituted alkyl, alkenyl, alkynyl, cycloalkyl, cycloalkenyl or phenyl;

$R^2$ is CN, $CONH_2$, $CSNH_2$, or haloalkyl;

$R^3$ is hydrogen or unsubstituted or substituted alkyl or cycloalkyl;

$R^4$ is alkoxy, unsubstituted or substituted alkyl, cycloalkenyl, cycloalkyl, alkenyl or alkynyl, an unsubstituted or substituted 5-membered or 6-membered heterocyclic radical or unsubstituted or substituted phenyl;

haloalkyl, alkoxy, haloalkoxy, alkylthio and/or haloalkylthio, and agriculturally useful salts of the isoxazole or isothiazole derivatives I, useful as herbicides.

10 Claims, No Drawings

ACYLAMINO-SUBSTITUTED ISOXAZOLE OR ISOTHIAZOLE DERIVATIVES, THEIR PREPARATION AND THEIR USE

The present invention relates to novel acylamino-substituted isoxazole or isothiazole derivatives of the formula I

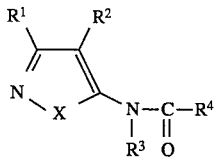

where

X is oxygen or sulfur, $R^1$ is $C_1$–$C_6$-alkyl which may carry from one to five halogen atoms and/or one cyano radical and/or up to two of the following radicals: $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, which in turn may be substituted by from one to three halogen or $C_1$–$C_4$-alkyl radicals, or phenyl which may furthermore carry from one to three of the following radicals: cyano, halogen, nitro, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio and $C_1$–$C_6$-haloalkylthio;

$C_2$–$C_6$-alkenyl, whose double bond may be epoxidized, or $C_2$–$C_6$-alkynyl, where both groups may be monosubstituted to trisubstituted by halogen or $C_1$–$C_3$-alkoxy and/or monosubstituted by cyclopropyl or phenyl, where the phenyl radical may additionally carry from one to three of the following substituents: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio;

$C_3$–$C_8$-cycloalkyl or $C_3$–$C_6$-cycloalkenyl, where both groups may be monosubstituted to trisubstituted by $C_1$–$C_4$-alkyl and/or by halogen;

phenyl which may furthermore carry from one to three of the following radicals: cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio and $C_1$–$C_6$-haloalkylthio;

$R^2$ is CN, $CONH_2$, $CSNH_2$, SCN or $C_1$–$C_2$-haloalkyl;

$R^3$ is hydrogen;

$C_1$–$C_6$-alkyl which may carry from one to three of the following substituents: hydroxyl, halogen, $C_1$–$C_4$-alkoxy and/or $C_1$–$C_4$-alkylthio;

$C_3$–$C_8$-cycloalkyl which may be monosubstituted to trisubstituted by halogen, $C_1$–$C_4$-alkyl and/or $C_1$–$C_4$-haloalkyl;

$R^4$ is $C_1$–$C_4$-alkoxy;

$C_1$–$C_6$-alkyl which may carry from one to three of the following radicals: halogen, cyano, $C_1$–$C_4$-alkoxy, $C_1$–$C_4$-haloalkoxy, $C_1$–$C_4$-alkylthio, $C_1$–$C_4$-haloalkylthio, $C_3$–$C_8$-cycloalkyl or phenyl, where the phenyl ring in turn may carry from one to three of the following radicals: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and/or $C_1$–$C_4$-haloalkylthio;

$C_3$–$C_8$-cycloalkenyl which may be monosubstituted to trisubstituted by halogen or by $C_1$–$C_4$-alkyl;

$C_3$–$C_6$-cycloalkyl which may carry from one to three of the following radicals: halogen, nitro, cyano, $C_1$–$C_6$-alkyl, $C_1$–$C_6$-haloalkyl, $C_1$–$C_4$-alkoxy and/or $C_1$–$C_4$-haloalkoxy;

$C_3$–$C_6$-alkenyl or $C_3$–$C_6$-alkynyl, each of which may be monosubstituted to trisubstituted by halogen and/or monosubstituted by phenyl, where the phenyl radical in turn may carry from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

a 5-membered or 6-membered heterocyclic saturated or aromatic radical having one or two hetero atoms selected from the group consisting of oxygen, sulfur and nitrogen, which may be monosubstituted to trisubstituted by $C_1$–$C_4$-alkyl or by halogen; phenyl which may furthermore carry from one to three of the following radicals: cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio and/or $C_1$–$C_6$-haloalkylthio;

and agriculturally useful salts of the isoxazole or isothiazole derivatives I, with the exception of:

3-methyl-4-thiocyanato-5-trifluoroacetylaminoisoxazole,
3-methyl-4-thiocyanato-5-benzoylaminoisoxazole,
3-methyl-4-cyano-5-fur-2-ylcarbonylaminoisoxazole,
3-ethyl-4-cyano-5-fur-2-ylcarbonylaminoisoxazole,
3-methyl-4-cyano-5-benzoylaminoisothiazole,
3-methyl-4-carboxamido-5-acetylaminoisothiazole,
3-methyl-4-carboxamido-5-(4-chlorobenzoyl)-aminoisothiazole,
3-methyl-4-carboxamido-5-(2-chlorobenzoyl)-aminoisothiazole,
3-methyl-4-carboxamido-5-benzoylaminoisothiazole,
3-phenyl-4-cyano-5-benzoylaminoisoxazole,
3-phenyl-4-cyano-5-(4-chlorobenzoyl)-aminoisoxazole,
3-phenyl-4-cyano-5-(4-methylbenzoyl)-aminoisoxazole and
3-phenyl-4-cyano-5-propionylaminoisoxazole.

It is generally known that urea compounds have good herbicidal properties. According to K.H. Büchel, Pflanzenschutz und Schädlingsbekämpfung, Georg Thieme Verlag, Stuttgart 1977, pages 169–172, the herbicidal activity of this class of compounds is particularly good when trisubstituted ureas are present. Urea derivatives having heterocyclic substituents are described in, for example, DE-A 24 34 922.

It is also known that certain substituted isoxazole and isothiazole derivatives have herbicidal actions. Examples of such compounds are 3-chloro-4-cyano-5-pivaloylaminoisothiazole (DE-A 19 24 830) and 3-isopropoxy-4-cyano-5-isobuturylaminoisothiazole (U.S. Pat. No. 4,059,433).

However, the action of these compounds or their toleration by crops is not sufficient in every case.

Isoxazoles having fungicidal properties are disclosed in JP-A 59/128 306 (eg. 3-phenyl-4-chloro-5-chloroacetylaminoisoxazole) and EP-A 105 548 (eg. 3-phenyl-4-chloro-5-acetylaminoisoxazole).

Furthermore, the following compounds are described in the literature without any indication of herbicidal properties:

3-methyl-4-thiocyanato-5-trifluoroacetylaminoisoxazole and 3-methyl-4-thiocyanato-5-benzoylaminoisoxazole (Pestic. Sci. 34 (1992), 127), 3-methyl-4-cyano-5-fur-2-ylcarbonylaminoisoxazole and 3-ethyl-4-cyano-5-fur-2-ylcarbonylaminoisoxazole (U.S. Pat. No. 3,770,740 and J. Med. Chem. 17 (1974), 451, respectively), 3-methyl-4-cyano-5-benzoylaminoisothiazole (Chem. Ber. 96 (1963), 526), 3-methyl-4-carboxamido-5-acetylaminoisothiazole and 3-methyl-4-carboxamido-5-benzoylaminoisothiazole (Arch. Immunol. Ther. Exp. 21 (1973), 909; CA 80: 128066), 3-methyl-4-carboxamido-5-(4-chlorobenzoyl)-aminoisothiazole and 3-methyl-4-carboxamido-5-(2-chlorobenzoyl)-aminoisothiazole (Diss. Pharm. Pharmacol. 22 (1970), 395; CA 74: 87882), 3-phenyl-4-cyano-5-benzoylaminoisoxazole, 3-phenyl-4-cyano-5-(4-chlorobenzoyl)-aminoisoxazole, 3-phenyl-4-cyano-5-(4-methylbenzoyl)-aminoisoxazole and 3-phenyl-4-cyano-5-propionylaminoisoxazole (Tetrahedron 23 (1967), 687).

It is an object of the present invention to synthesize isoxazole and isothiazole derivatives having improved properties in particular with regard to activity and tolerance by crops. We have found that this object is achieved by the compounds of the general formula I which are defined at the outset.

The novel compounds of the formula I can be prepared by various methods.

We have found that the novel isoxazole or isothiazole derivatives of the formula I

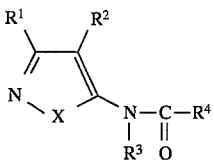

where $R^3$ is alkyl or cycloalkyl and X, $R^1$, $R^2$ and $R^4$ have the meanings stated at the outset, are obtained by reacting a compound of the formula II

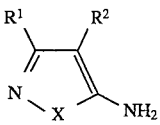

where X, $R^1$ and $R^2$ have the abovementioned meanings, first with a carbonyl chloride of the formula III

where $R^4$ has the abovementioned meanings, or with another activated derivative of a carboxylic acid, such as the anhydride, to give a compound of the formula IV (reaction step A)

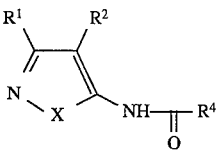

and this is reacted with an alkyl or cycloalkylhalogen compound of the formula V

where $R^3$ is unsubstituted or substituted alkyl or cycloalkyl as stated above and Hal is halogen, eg. chlorine or bromine, or with a sulfate of the formula VI

in the presence or absence of a base (reaction step B).

The individual reaction steps may be carried out as follows:

Reaction step A:

In an advantageous procedure, the reactants in an inert organic solvent or solvent mixture are reacted at from $-20°$ C. to the boiling point of the solvent, in the presence or absence of a base. The ratio of amine II to activated carboxylic acid III may be from 2.5:1 to 1:3. If, for example, a carbonyl chloride is used an equimolar amount or in excess, it is useful to carry out the reaction in the presence of an auxiliary base. For example, amines, such as triethylamine or pyridine, or alkali metal or alkaline earth metal hydroxides are suitable for this purpose. The addition of a catalytic amount of N,N-dimethylaminopyridine may also be advantageous. Suitable solvents for the reactions include hydrocarbons, such as benzene, toluene or xylene, halohydrocarbons, such as dichloroethane, and ethers, such as diethyl ether, tert-butyl methyl ether or tetrahydrofuran.

Reaction step B:

The alkylation of the antide is advantageously carried out by reacting the compound of the general formula IV in an aprotic organic solvent with an alkylating agent of the general formula V or VI at from $-10°$ to $+50$ C. in the presence of a base. The alkylating agent may be used in an equimolar amount or in excess, for example up to a two-fold excess. Suitable solvents are hydrocarbons, such as benzene, toluene or xylene, ethers, such as diethyl ether, tert-butyl methyl ether or tetrahydrofuran, halohydrocarbons, such as dichloromethane, dimethylsulfoxide (DMF) or dimethyl sulfoxide (DMSO). Suitable bases are alkali metal and alkaline earth metal carbonates, hydroxides or hydrides, such as sodium carbonate, potassium carbonate, sodium hydroxide, potassium hydroxide or sodium hydride, alcoholates, such as sodium methylate, or metal organyls, such as n-butyllithium.

Suitable alkylating agents are alkyl or cycloalkyl halides, eg. methyl iodide, or dimethyl sulfate.

A possible method for synthesizing compounds of the general formula I, where $R^2$ is $CONH_2$ and X, $R^1$, $R^3$ and $R^4$ have the abovementioned meanings, is to hydrolyze a nitrile of the general formula VII

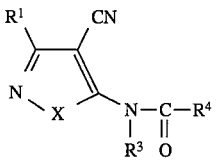

This hydrolysis can be carried out, for example, in an acidic medium. Acids, such as concentrated sulfuric acid, polyphosphoric acids, hydrogen chloride in formic acid or glacial acetic acid or boron trifluoride/glacial acetic acid, are suitable.

It is also possible to hydrolyze the nitriles in an alkaline medium to give the amides. Suitable reagents are $H2O_2$ with sodium hydroxide solution or sodium carbonate. This reaction can also advantageously be carried out under conditions of phase transfer catalysis. Potassium hydroxide/tert-butanol, ammonia, sodium peroxide/DMSO or a strongly alkaline ion exchanger may also be used. All hydrolyses are advantageously carried out at from $-20°$ to $100°$ C. The reagents are added in equimolar amounts or in excess. Very frequently, the hydrolyses are carried out in the absence of organic solvents. Under the conditions of phase transfer catalysis, halohydrocarbons, such as dichloromethane, are suitable solvents.

Compounds of the general formula I, where $R^2$ is $CSNH_2$ and X, $R^1$, $R^3$ and $R^4$ have the abovementioned meanings, are obtained by treating a nitrile of the general formula VII, in an organic solvent, with hydrogen sulfide at from 0 to 100° C. and atmospheric or superatmospheric pressure, in the presence or absence of a catalytic or equimolar amount of a nitrogen base. Suitable solvents for this reaction are alcohols, such as methanol, ethanol or isopropanol, ethers, aromatic hydrocarbons, such as benzene, toluene or xylene, pyridine or other polar solvents, eg. N-methylpyrrolidone. Tertiary amines, eg. triethylamine or pyridine, may be used as bases.

Compounds of the general formula I, where $R^2$ is SCN and X, $R^1$, $R^3$ and $R^4$ have the abovementioned meanings, are obtained by converting an isoxazole or isothiazole of the formula VIII

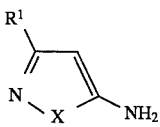                                    VIII by means of a halogenating agent into a halogen compound IX

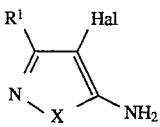                                    IX (reaction step A) and then converting this by reaction with a thiocyanate into a compound X (reaction step B)

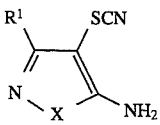                                    X

The acylation to give the desired products of the formula I, where $R^2$ is SCN and X, $R^1$, $R^3$ and $R^4$ have the abovementioned meanings, can be carried out by the methods described in the above processes.

The individual reaction steps can be carried out as follows:

Reaction step A:

The halogenation of the compounds of the formula VIII can be carried out by generally known methods, for example by initially taking VIII in a protic solvent, eg. glacial acetic acid, or in an aprotic solvent, such as an ether, an aromatic hydrocarbon or a halohydrocarbon, etc., and reacting it with the halogenating agent at from −10° to 50° C. The halogenating agent used may be, for example, bromine, chlorine or sulfuryl chloride, which may be employed in an equimolar amount or in excess.

Reaction step B:

The thiocyanate is obtained by reacting the halogen compound IX with an inorganic thiocyanate. The reaction is preferably carried out in an alcohol, such as methanol or ethanol, at from 25° C. to the boiling point. Preferred thiocyanates are sodium thiocyanate and potassium thiocyanate. They may be used in equimolar amounts or in excess. A variant of this reaction sequence is described in Pestic. Sci. 34 (1992), 127.

With regard to the novel herbicidal activity, the substituents in the compounds I have, for example, the following meanings:

X is oxygen or sulfur;

$R^1$ is straight-chain or branched $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl, ethyl, propyl, 1-methylethyl or 1,1-dimethylethyl, which may carry from one to five halogen atoms, such as fluorine, chlorine, bromine or iodine, in particular fluorine or chlorine, and/or one cyano radical and/or up to two of the following radicals:

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy;

partially or completely halogenated $C_1$–$C_4$-alkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy or pentafluoroethoxy;

$C_1$–$C_4$-alkylthio, such as methylthio, ethylthio, propylthio, 1-methylethylthio, n-butylthio, 1-methylpropylthio, 2-methylpropylthio or 1,1-dimethylethylthio, in particular methylthio or ethylthio;

partially or completely halogenated $C_1$–$C_4$-alkylthio, such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio or pentafluoroethylthio, in particular trifluoromethylthio or pentafluoroethylthio;

$C_3$–$C_8$-cycloalkyl, such as cyclopropyl, cyclobutyl, cyclopentyl, cyclohexyl, cycloheptyl or cyclooctyl, in particular cyclopropyl, cyclopentyl or cyclohexyl, where the cyclic structure may furthermore be monosubstituted to trisubstituted by $C_1$–$C_4$-alkyl as stated above, in particular methyl or ethyl, or by halogen, such as fluorine, chlorine, bromine or iodine, in particular fluorine or chlorine;

phenyl which may furthermore carry from one to three of the following radicals: cyano; nitro; halogen, such as fluorine, chlorine, bromine or iodine, in particular fluorine or chlorine; $C_1$–$C_6$-alkyl as stated above, in particular methyl, ethyl or 1-methylethyl; partially or completely halogenated $C_1$–$C_6$-alkyl as stated above, in particular trifluoromethyl or chlorodifluoromethyl; $C_1$–$C_6$-alkoxy as stated above, in particular methoxy or ethoxy; partially or completely halogenated $C_1$–$C_6$-alkoxy as stated above, in particular trifluoromethoxy, trichloromethoxy or pentafluoroethoxy; $C_1$–$C_4$-alkylthio as stated above, in particular methylthio or ethylthio, and/or partially or completely halogenated $C_1$–$C_6$-alkylthio as stated above, in particular difluoromethylthio, trifluoromethylthio or pentafluoromethylthio;

$R^1$ is furthermore $C_2$–$C_6$-alkenyl whose double bond may be epoxidized, preferably $C_2$–$C_4$-alkenyl, such as ethenyl, prop-2-en-1-yl, 1-methylethenyl, but-2-en-1-yl or 1-methylprop-2-en-1-yl, each of which may be monosubstituted to trisubstituted by halogen, such as fluorine, chlorine, bromine or iodine, or by $C_1$–$C_3$-alkoxy, such as methoxy, ethoxy or isopropoxy, and/or monosubstituted by cyclopropyl or phenyl, where the phenyl radical in turn may carry from one to three of the following groups: cyano, nitro, alkyl as stated above, in particular methyl, ethyl or 1-methylethyl; haloalkyl as stated above, in particular trifluoromethyl or chlorodifluoromethyl; alkoxy as stated above, in particular methoxy or ethoxy; haloalkoxy as stated above, in particular trifluoromethoxy, trichloromethoxy or pentafluoroethoxy; alkylthio as stated above, in particular methylthio or ethylthio; partially or completely halogenated alkylthio as stated above, in particular difluoromethylthio, trifluoromethylthio or pentafluoromethylthio, or halogen as stated above, in particular fluorine or chlorine;

$R^1$ may furthermore be $C_2$–$C_6$-alkynyl, preferably $C_2$–$C_4$-alkynyl, such as ethynyl, propyn-1-yl, 1-methyl-2-propynyl or n-butynyl, each of which may be monosubstituted to trisubstituted by halogen, such as fluorine, chlorine, bromine or iodine, or by $C_1$–$C_3$-alkoxy, such as methoxy or isopropoxy, and/or monosubstituted by cyclopropyl or phenyl, where the phenyl radical in turn may carry from one to three of the following groups: cyano, nitro, alkyl as stated above, in particular methyl, ethyl or 1-methylethyl; haloethyl as stated above, in particular trifluoromethyl or chlorodifluoromethyl; alkoxy as stated above, in particular methoxy or ethoxy; haloalkoxy as stated above, in particular trifluoromethoxy, trichloromethoxy or pentafluoroethoxy; alkylthio as stated above, in particular methylthio or ethylthio; partially or completely halogenated alkylthio as stated above, in particular difluoromethylthio, trifluoromethylthio or pentafluoromethylthio, or halogen as stated above, in particular fluorine or chlorine;

$R^1$ may furthermore be $C_3$–$C_8$-cycloalkyl, such as cyclopropyl, cyclobutyl, cyclopentyl, cyclohexyl, cycloheptyl or cyclooctyl, in particular cyclopropyl, cyclopentyl or cyclohexyl, or $C_3$–$C_6$-cycloalkenyl, in particular $C_5$– or $C_6$-cycloalkenyl, such as cyclohexen-1-yl, where the cyclic structure may furthermore be monosubstituted to trisubstituted by $C_1$–$C_4$-alkyl as stated above, in particular methyl or ethyl, or by halogen, such as fluorine, chlorine, bromine or iodine, in particular fluorine or chlorine;

$R^1$ may furthermore be phenyl which may also carry from one to three of the following radicals: cyano, nitro, halogen, such as fluorine, chlorine, bromine or iodine, in particular fluorine or chlorine; $C_1$–$C_6$-alkyl as stated above, in particular methyl, ethyl or 1-methylethyl; partially or completely halogenated $C_1$–$C_6$-alkyl as stated above, in particular trifluoromethyl or chlorodifluoromethyl; $C_1$–$C_6$-alkoxy as stated above, in particular methoxy or ethoxy; partially or completely halogenated $C_1$–$C_6$-alkoxy as stated above, in particular trifluoromethoxy, trichloromethoxy or pentafluoroethoxy; $C_1$–$C_4$-alkylthio as stated above, in particular methylthio or ethylthio, and/or partially or completely halogenated $C_1$–$C_6$-alkylthio as stated above, in particular difluoromethylthio, trifluoromethylthio or pentafluoromethylthio;

$R^2$ is CN, $CONH_2$, $CSNH_2$, SCN or $C_1$– or $C_2$-haloalkyl, such as trifluoromethyl or trichloromethyl, in particular CN, $CONH_2$ or $CSNH_2$;

$R^3$ is hydrogen;

$C_1$–$C_6$-alkyl, preferably $C_1$–$C_4$-alkyl, such as methyl, ethyl or tert-butyl, which may carry from one to three of the following substituents: hydroxyl, halogen, $C_1$–$C_4$-alkoxy, such as methoxy or tert-butoxy, or $C_1$–$C_4$-alkylthio, such as methylthio or tert-butylthio;

$C_3$–$C_8$-cycloalkyl, preferably $C_5$– or $C_6$-cycloalkyl, such as cyclopentyl or cyclohexyl, which may be monosubstituted to trisubstituted by halogen, such as fluorine, chlorine or bromine, $C_1$–$C_4$-alkyl, such as methyl or tert-butyl, or partially or completely halogenated $C_1$–$C_4$-alkyl, such as fluoromethyl, trifluoromethyl, chlorodifluoromethyl, pentafluoroethyl or 2-chloro-1,1,2-trifluoroethyl;

$R^4$ is $C_1$–$C_4$-alkoxy as stated above, in particular methoxy, ethoxy or isopropoxy;

branched or straight-chain $C_1$–$C_6$-alkyl, preferably $C_2$–$C_4$-alkyl, such as ethyl, isopropyl or tert-butyl, which may carry from one to three of the following radicals: halogen, such as fluorine, chlorine or bromine, cyano, $C_1$–$C_4$-alkoxy, such as methoxy or tert-butoxy, partially or completely halogenated $C_1$–$C_4$-alkoxy, such as fluoromethoxy, trichloromethoxy, 2-chloro-1,1,2-trifluoroethoxy or pentafluoroethoxy, $C_1$–$C_4$-alkylthio, such as methylthio or tert-butylthio, $C_1$–$C_4$-haloalkylthio, such as fluoromethylthio, trichloromethylthio, 2-chloro-1,1,2-trifluoroethylthio or pentafluoroethylthio, $C_3$–$C_8$-cycloalkyl, in particular $C_3$–$C_6$-cycloalkyl, such as cyclopropyl, cyclopentyl and cyclohexyl, or phenyl, where the phenyl radical in turn may carry from one to three of the following groups: halogen, such as fluorine, chlorine or bromine, cyano, nitro, $C_1$–$C_4$-alkyl, such as methyl or tert-butyl, $C_1$–$C_4$-haloalkyl, such as fluoromethyl, trichloromethyl, 2-chloro-1,1,2-trifluoroethyl or pentafluoroethyl, $C_1$–$C_4$-alkoxy, such as methoxy or tert-butoxy, partially or completely halogenated $C_1$–$C_4$-alkoxy, such as fluoromethoxy, trichloromethoxy, 2-chloro-1,1,2-trifluoroethoxy or pentafluoroethoxy, $C_1$–$C_4$-alkylthio, such as methylthio or tert-butylthio, or $C_1$–$C_4$-haloalkylthio, such as fluoromethylthio, trichloromethylthio, 2-chloro-1,1,2-trifluoroethylthio or pentafluoroethylthio;

$R^4$ may furthermore be $C_3$–$C_8$-cycloalkyl, preferably $C_3$–$C_6$-cycloalkyl, in particular cyclopropyl, cyclopentyl or cyclohexyl, each of which may carry from one to three of the following radicals: halogen, such as fluorine, chlorine or bromine, nitro, cyano, $C_1$–$C_6$-alkyl, preferably $C_1$–$C_4$-alkyl, such as methyl or tert-butyl, partially or completely halogenated $C_1$–$C_6$-alkyl, preferably $C_1$–$C_4$-haloalkyl, such as fluoromethyl, trichloromethyl, 2-chloro-1,1,2-trifluoroethyl or pentafluoroethyl, $C_1$–$C_4$-alkoxy, such as methoxy or tert-butoxy, or partially or completely halogenated $C_1$–$C_4$-alkoxy, such as fluoromethoxy, trichloromethoxy, 2-chloro-1,1,2-trifluoroethoxy or pentafluoroethoxy;

$C_3$–$C_6$-cycloalkenyl, preferably $C_5$– or $C_6$-cycloalkenyl, which may be monosubstituted to trisubstituted by halogen, such as fluorine, chlorine, bromine or iodine, in particular fluorine or chlorine, or $C_1$–$C_4$-alkyl, such as methyl, ethyl or tert-butyl;

$R^4$ may furthermore be $C_3$–$C_6$-alkenyl or $C_3$–$C_6$-alkynyl, preferably $C_3$– or $C_4$-alkenyl or $C_3$–$C_6$-alkynyl, such as 2-propenyl, 2-butenyl, 2-propynyl, 1,1-dimethyl-2-propynyl or 3-butynyl, each of which may be monosubstituted to trisubstituted by halogen, such as fluorine, chlorine or bromine, and/or monosubstituted by phenyl, where the phenyl radical in turn may carry from one to three of the following substituents: halogen, in particular fluorine or chlorine, cyano, nitro, $C_1$–$C_4$-alkyl, such as methyl or tert-butyl, partially or completely halogenated $C_1$–$C_4$-alkyl, such as fluoromethyl, trifluoromethyl, trichloromethyl, 2-chloro-1,1,2-trifluoroethyl or pentafluoroethyl, $C_1$–$C_4$-alkoxy, such as methoxy or tert-butoxy, $C_1$–$C_4$-haloalkoxy, such as fluoromethoxy, trifluoromethoxy, trichloromethoxy, 2-chloro-1,1,2-trifluoroethoxy or pentafluoroethoxy, $C_1$–$C_4$-alkylthio, such as methylthio or tertbutylthio, partially or completely halogenated $C_1$–$C_4$-alkylthio, such as fluoromethylthio, trifluoromethylthio, trichloromethylthio, 2-chloro-1,1,2-trifluoroethylthio or pentafluoroethylthio;

$R^4$ may furthermore be a 5-membered or 6-membered saturated or aromatic heterocyclic radical containing one or two hetero atoms selected from the group consisting of oxygen, sulfur and nitrogen, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl or 4-pyridyl, which may carry from one to three of the following substituents: $C_1$–$C_4$-alkyl as stated above, in particular methyl, or halogen as stated above, in particular fluorine or chlorine;

$R^4$ may furthermore be phenyl which may also carry from one to three of the following radicals: cyano; nitro; halogen, such as fluorine, chlorine, bromine or iodine, in particular fluorine or chlorine; $C_1$–$C_6$-alkyl as stated above, in particular methyl, ethyl or 1-methylethyl; partially or completely halogenated $C_1$–$C_6$-alkyl as stated above, in particular trifluoromethyl or chlorodifluoromethyl; $C_1$–$C_6$-alkoxy as stated above, in particular methoxy or ethoxy; partially or completely halogenated $C_1$–$C_6$-alkoxy as stated above, in particular trifluoromethoxy, trichloromethoxy or pentafluoroethoxy; $C_1$–$C_4$-alkylthio as stated above, in particular methylthio or ethylthio, and/or partially or completely halogenated $C_1$–$C_6$-alkylthio as stated above, in particular difluoromethylthio, trifluoromethylthio or pentafluoromethylthio.

Isoxazole and isothiazole derivatives of the formula I, where $R^1$ is alkyl, alkenyl or alkynyl, each of 2 to 6 carbon atoms, $C_3$–$C_8$-cycloalkyl or $C_3$–$C_6$-cycloalkenyl, each of which may be substituted as stated above, are particularly preferred. $R^1$ may also advantageously be a substituted methyl group, suitable substituents being from one to three halogen atoms, such as fluorine, chlorine or bromine, and/or cyano and/or one or two of the following radicals:

$C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, which in turn may be substituted by from one to three halogen and/or alkyl radicals, or phenyl, which may furthermore carry from one to three of the following radicals: cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio or $C_1$–$C_6$-haloalkylthio Preferred radicals $R^2$ are cyano, $CONH_2$ and $CSNH_2$, and preferred radicals $R^3$ are hydrogen or $C_1$–$C_6$-alkyl, in particular $C_1$–$C_4$-alkyl.

$R^4$ is preferably $C_1$–$C_4$-alkoxy, unsubstituted or substituted $C_1$–$C_6$-alkyl or $C_3$–$C_8$-cycloalkyl.

The agriculturally useful salts of I are also a subject of the present invention. Usually, the type of salt is not important here. In general, the salts of those bases and those esters which do not adversely affect the herbicidal action of the compounds I are suitable.

Agriculturally useful salts of the compounds I are, for example, alkali metal salts, in particular sodium salts and potassium salts, alkaline earth metal salts, in particular calcium salts, magnesium salts and barium salts, manganese salts, copper salts, zinc salts or iron salts and ammonium salts, such as tetraalkyl- and benzyltrialkylammonium salts, phosphonium salts, sulfonium salts, such as trialkylsulfonium salts, or sulfoxonium salts.

The salts of the compounds I are obtainable in a manner known per se (EP-A--304 282, U.S. Pat. No. 4,599,412). They are obtained by deprotonation of the corresponding compounds I in water or in an inert organic solvent at from –80° to 120° C., preferably from 0° to 60° C., in the presence of a base.

Examples of suitable bases are alkali metal or alkaline earth metal hydroxides, hydrides, oxides or alcoholates, such as sodium hydroxide, potassium hydroxide and lithium hydroxide, sodium methylate, ethylate and tert-butylate, sodium hydride, calcium hydride and calcium oxide.

Examples of suitable solvents in addition to water are alcohols, such as methanol, ethanol and tert-butanol, ethers, such as tetrahydrofuran and dioxane, acetonitrile, dimethylformamide, ketones, such as acetone and methyl ethyl ketone, and halohydrocarbons.

The deprotonation may be carried out at atmospheric pressure or at up to 50 bar, preferably at from atmospheric pressure to 5 bar gauge pressure.

The compounds I or the herbicides containing them, and the environmentally compatible salts thereof, for example of alkali metals and alkaline earth metals, are capable of controlling weeds very well in crops such as wheat, rice, corn, soybean and cotton, without damaging the crops, an effect which occurs in particular at low application rates. They can be used, for example, in the form of directly sprayable solutions, powders, suspensions, including concentrated aqueous, oily or other suspensions or dispersions, emulsions, oil dispersions, pastes, dusts, broadcasting agents or granules, by spraying, nebulizing, dusting, broadcasting or pouring. The application forms depend on the intended uses; they should in any case ensure very fine distribution of the novel active ingredients.

The compounds I are suitable in general for the preparation of directly sprayable solutions, emulsions, pastes or oil dispersions. Suitable inert additives include mineral oil fractions having a medium to high boiling point, such as kerosine or diesel oil, as well as coal-tar oils and oils of vegetable or animal origin, aliphatic, cyclic and aromatic hydrocarbons, eg. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substances, as such or dissolved in an oil or solvent, can be homogenized in water by means of wetting agents, adherents, dispersants or emulsifiers. However, it is also possible to prepare concentrates which consist of active substance, wetting agents, adherents, dispersants or emulsifiers and possibly solvents or oil and which are suitable for dilution with water.

Suitable surfactants are the alkali metal, alkaline earth metal and ammonium salts of aromatic sulfonic acids, for example lignin-, phenol-, naphthalene- and dibutylnaphthalenesulfonic acid, and of fatty acids, alkylsulfonates and alkylarylsulfonates, alkylsulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenol polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene, lauryl alcohol polyglycol ether acetate, sorbitol esters, ligninsulfite waste liquors or methylcellulose.

Powders, broadcasting agents and dusts can be prepared by mixing or milling the active substances together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders and other solid carriers.

The formulations contain in general from 0.01 to 95, preferably from 0.5 to 90% by weight of active ingredient. The active ingredients were used in a purity of from 90 to 100%, preferably from 95 to 100% (according to the NMR spectrum).

Examples of formulations are:

I. 20 parts by weight of compound No. 1.001 are dissolved in a mixture which consists of 80 parts by weight of xylene, 10 parts by weight of the adduct of from 8 to 10 mol of ethylene oxide with 1 mol of N-monoethanol oleamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

II. 20 parts by weight of compound No. 1.002 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of active ingredient No. 1.003 are dissolved in a mixture which consists of 25 parts by weight of cyclohexanone, 65 parts by weight of a mineral oil fraction boiling within a range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. 1,001 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

V. 3 parts by weight of active ingredient No. 1.002 are mixed with 97 parts by weight of finely divided kaolin. A dust which contains 3% by weight of the active ingredient is obtained in this manner.

VI. 20 parts by weight of active ingredient No. 1.003 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

Application may be effected by the preemergence or postemergence method. If the active ingredients are less well tolerated by certain crops, it is possible to use application methods in which the herbicides are sprayed with the aid of the sprayers in such a way that the leaves of the sensitive crops are as far as possible not affected, while the active ingredients reach the leaves of undesirable plants growing underneath or the uncovered soil surface (post-directed, lay-by).

The application rates of active ingredient are from 0.001 to 2, preferably from 0.01 to 1, kg/ha of active substance (a.s.), depending on the aim of control, the season, the target plants and the stage of growth.

In view of the versatility of the application methods, the novel compounds or agents containing them may also be used in a further number of crops for eliminating undesirable plants. For example, the following crops are suitable:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Beta vulgaris spp. altissima* | sugarbeets |
| *Beta vulgaris spp. rapa* | fodder beets |
| *Brassica napus var. napus* | rapeseed |
| *Brassica napus var. napobrassica* | swedes |
| *Brassica rapa var. silvestris* | beets |
| *Camellia sinensis* | tea plants |
| *Carthamus tinctorius* | safflower |
| *Citrus limon* | lemons |
| *Citrus sinensis* | orange trees |
| *Coffea arabica* (coffee canephora, *Coffea liberica*) | coffee plants |
| *Cucumis sativus* | cucumbers |
| *Cynodon dactylon* | Bermudagrass in turf and lawns |
| *Daucus carota* | carrots |
| *Elaeis guineensis* | oil palms |
| *Fragaria vesca* | strawberries |
| *Glycine max* | soybeans |
| *Gossypium hirsutum* (*Gossypium arboreum*, *Gossypium herbaceum*, *Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus spp.* | apple trees |
| *Manihot esculenta* | cassava |
| *Medicago sativa* | alfalfa (lucerne) |
| *Musa spp.* | banana plants |
| *Nicotiana tabacum* (*N. rustica*) | tobacco |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus spp.* | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (*S. vulgare*) | sorghum |
| *Theobroma cacao* | cacao plants |
| *Trifolium pratense* | red clover |
| *Triticum aestivum* | wheat |
| *Triticum durum* | durum wheat |
| *Vicia faba* | tick beans |
| *Vitis vinifera* | grapes |
| *Zea mays* | Indian corn, sweet corn, maize |

In order to broaden the action spectrum and to achieve synergistic effects, the acylamino-substituted isoxazole or isothiazole derivatives of the formula I can be mixed with many members of other groups of herbicidal or growth-regulating active ingredients and applied together with them. Suitable components of the mixture are, for example, diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives which carry, for example, a carboxyl or carbimino group in the 2 position, imidazolinones, sulfonamides, sulfonylureas, quinolinecarboxylic acid derivatives, aryloxy- and hetaryloxyphenoxypropionic acids and their salts, esters and amides and others.

It may also be useful to apply the compounds of the formula I, alone or in combination with other herbicides, also as a mixture together with further crop protection agents, for example with pesticides or with agents for controlling phytopathogenic fungi or bacteria. The miscibility with mineral salt solutions which are used for eliminating nutrient and trace element deficiencies is also of interest. Nonphytotoxic oils and oil concentrates may also be added.

Typical examples of the preparation of the intermediates V are described below.

PREPARATION EXAMPLES

5-Cyclopropylcarbonylamino-3-isopropylisothiazole-4-carbonitrile 12.5 g of cyclopropanecarbonyl chloride in 30 ml of toluene are added dropwise to a solution of 16.7 g of 5-amino-4-cyano-3-isopropylisothiazole and about 0.5 g of DMAP (N,N-dimethylaminopyridine) in 200 ml of toluene and 200 ml of pyridine. The solution is stirred for 16 hours at room temperature and then evaporated to dryness, and the residue is taken up in ethyl acetate. The organic phase is extracted with aqueous sodium bicarbonate solution and 10% strength hydrochloric acid and is dried and evaporated down.

Yield: 22.3 g, mp. 193° C.

3-Ethyl-5-(4-chlorobutanoyl)aminoisothiazole-4-carboxamide 5 g of 3-ethyl-5-(4-chlorobutanoyl)aminoisothiazole-5-carbonitrile in 30 ml of concentrated sulfuric acid are stirred for 12 hours at room temperature. The solution is then stirred in 250 ml of ice water, rendered weakly alkaline with concentrated ammonia solution and extracted with dichloromethane. The organic phase is dried and evaporated down.

Yield: 3.3 g, mp. 97° C.

5-(2-Methylbutanoyl)amino-3-isopropylisothiazole-4-thiocarboxamide 8.5 g of 5-(2-methylbutanoyl)amino-3-isopropylisothiazole- 4-carbonitrile and 3.4 g of triethylamine in about 60 ml of N-methylpyrrolidone are initially taken and treated with $H_2S$ gas at 60° C. for several hours. Thereafter, the solution is allowed to cool and is poured onto 1.5 l of water, and the product is filtered off.

Yield: 8.8 g, mp. 132°–133° C.

5-(3-Methylbutanoyl)amino-3-isopropylisoxazole-4-carboxamide 1.7 g of 5-amino-3-isopropylisoxazole-4-carboxamide in a mixture of 40 ml of toluene and 40 ml of pyridine are initially taken together with a pinch of dimethylaminopyridine, and a solution of 2.5 g of isovaleroyl chloride in 20 ml of toluene is added. Stirring is carried out for 16 hours at room temperature, after which the solution is evaporated to dryness and the residue is stirred with ethyl acetate. The organic phase is then extracted with aqueous hydrochloric acid and sodium bicarbonate solution, dried and evaporated down. Purification is effected by chromatography over silica gel (cyclohexane/ethyl acetate).

Yield: 0.2 g $^1$H-NMR (DMSO-$d_6$), δ in ppm: 0.95 (d, 6 H); 1.25(d, 6 H); 2.05(m, 1 H); 2.25(d, 2 H); 3.30(m, 1 H); 7.40(br, 2 H); 10.8(s, 1 H).

3-Methyl-4-isothiocyanato-5-pivaloylaminoisothiazole 16.7 g of 5-amino-4-isothiocyanato-3-methylisothiazole and 0.5 g of dimethylaminopyridine are dissolved in a mixture of 100 ml of toluene and 100 ml of pyridine, and 15.9 g of pivaloyl chloride are added. Stirring is carried out for 16 hours at 80° C., the solution is evaporated to dryness, the residue is taken up in ethyl acetate and the solution is extracted with aqueous sodium bicarbonate solution and 10% strength hydrochloric acid. The organic phase is dried and evaporated down.

Yield: 28 g, mp. 98°–100° C.

3-Methyl-4-thiocyanato-5-aminoisothiazole 386 g of 3-methyl-4-bromo-5-aminoisothiazole and 200 g of KSCN in methanol are refluxed for 6 hours. The product crystallizes out on cooling. 800 ml of water are added and the product is filtered off under suction and washed with water.

Yield: 328 g, mp. 150°–151° C.

The compounds I shown in the table below were obtained in a similar manner.

Active ingredients table

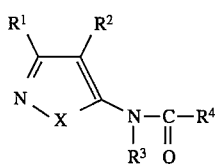

| No. | R$^1$ | R$^2$ | R$^3$ | R$^4$ | X | phys. data mp./$^1$H-NMR [°C.]/δ[ppm] |
|---|---|---|---|---|---|---|
| 1.001 | C$_6$H$_5$ | CN | H | CH$_2$Cl | S | |
| 1.002 | CH$_2$C$_6$H$_5$ | CONH$_2$ | H | CH$_3$ | S | |
| 1.003 | CHCl$_2$ | CN | H | C$_2$H$_5$ | S | |
| 1.004 | CCl$_2$C$_6$H$_5$ | CN | H | C$_2$H$_5$ | S | |
| 1.005 | CH(CH$_3$)$_2$ | CN | H | C(CH$_3$)$_2$C$_3$H$_7$ | S | 95–96 |

-continued

Active ingredients table

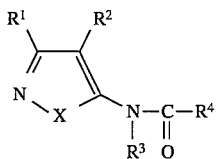

| No. | $R^1$ | $R^2$ | $R^3$ | $R^4$ | X | phys. data mp./$^1$H-NMR [°C.]/δ[ppm] |
|---|---|---|---|---|---|---|
| 1.006 | $CH(CH_3)_2$ | CN | H | $C_4H_7$ | S | 140–141 |
| 1.007 | $CH(CH_3)_2$ | CN | H | $CH_2C(CH_3)_3$ | S | 148–151 |
| 1.008 | $CH(CH_3)_2$ | CN | H | $CCl_3$ | S | 97–98 |
| 1.009 | $C_6H_5$ | CN | H | $C_3H_5$ | S | 157–161 |
| 1.010 | $CH_2C_6H_5$ | CN | H | $C_3H_5$ | S | 196–199 |
| 1.011 | $CH_2C_6H_5$ | CN | H | $C_6H_5$ | S | 187–189 |
| 1.012 | $CH(CH_3)_2$ | CN | H | $CH_3$ | S | 175–176 |
| 1.013 | $CH_3$ | CN | H | $CH_3$ | O | 198–200 |
| 1.014 | $C_3H_7$ | CN | H | $CH_3$ | S | 195–196 |
| 1.015 | $C_3H_7$ | CN | H | $C_2H_5$ | S | 158–159 |
| 1.016 | $C_3H_7$ | CN | H | $CH(CH_3)_2$ | S | 135–136 |
| 1.017 | $CH(CH_3)_2$ | CN | H | $C_3H_7$ | S | 128–130 |
| 1.018 | $CH(CH_3)_2$ | CN | H | $C_6H_5$ | S | 156–157 |
| 1.019 | $CH(CH_3)_2$ | CN | H | $OC_2H_5$ | S | 155–158 |
| 1.020 | $CH(CH_3)_2$ | CN | H | $C_3H_5$ | S | 194–195 |
| 1.021 | $CH(CH_3)_2$ | CN | H | $CH_2CH_2CH_2Cl$ | S | 123–124 |
| 1.022 | $CH(CH_3)_2$ | CN | H | $CH(CH_3)C_2H_5$ | S | 83–87 |
| 1.023 | $CH(CH_3)_2$ | CN | H | $CH_2CH(CH_3)_2$ | S | 127–128 |
| 1.024 | $CH_3$ | CN | H | $C_3H_5$ | S | 237–240 |
| 1.025 | $CH_3$ | CN | H | $CH_3$ | S | 203–205 |
| 1.026 | $CH_3$ | CN | H | $CH(CH_3)C_2H_5$ | S | 92–94 |
| 1.027 | $CH_3$ | CN | H | $CH_2CH(CH_3)_2$ | S | 157–158 |
| 1.028 | $CH_3$ | CN | H | $CH_2CH_2CH_2Cl$ | S | 186–187 |
| 1.029 | $CH_3$ | CN | H | $C_3H_7$ | S | 168–172 |
| 1.030 | $C_2H_5$ | CN | H | $C_6H_5$ | S | 189–199 |
| 1.031 | $C_2H_5$ | CN | H | $OC_2H_5$ | S | 152–154 |
| 1.032 | $C_2H_5$ | CN | H | $C_3H_5$ | S | 226–227 |
| 1.033 | $C_2H_5$ | CN | H | $C(CH_3)_3$ | S | 98–101 |
| 1.034 | $C_2H_5$ | CN | H | $CH(CH_3)C_2H_5$ | S | 104–106 |
| 1.035 | $C_2H_5$ | CN | H | $CH_2CH(CH_3)_2$ | S | 165–170 |
| 1.036 | $C_2H_5$ | CN | H | $CH_2CH_2CH_2Cl$ | S | 169 |
| 1.037 | $C_2H_5$ | CN | H | $C_3H_7$ | S | 170 |
| 1.038 | $CH_3$ | CN | H | $C(CH_3)_3$ | S | 142–147 |
| 1.039 | $CH(CH_3)_2$ | CN | H | $4\text{-Cl}-C_6H_4$ | S | 199 |
| 1.040 | $CH(CH_3)_2$ | CN | H | $3\text{-Cl}-C_6H_4$ | S | 110–112 |
| 1.041 | $CH(CH_3)_2$ | CN | H | $3\text{-CH}_3-C_6H_4$ | S | 128–129 |
| 1.042 | $CH(CH_3)_2$ | CN | H | $C_6H_{11}$ | S | 124–125 |
| 1.043 | $CH(CH_3)_2$ | CN | H | $CH(CH_3)_2$ | S | 101–103 |
| 1.044 | $CH(CH_3)_2$ | CN | H | $C(CH_3)_3$ | S | 125–126 |
| 1.045 | $CH(CH_3)_2$ | CN | H | $C_2H_5$ | S | 187–188 |
| 1.046 | $CH_3$ | CN | H | $CH(CH_3)_2$ | O | 144–145 |
| 1.047 | $CH_3$ | CN | H | $C(CH_3)_3$ | O | 197–198 |
| 1.048 | $CH(CH_3)_2$ | CN | H | $CH(CH_3)_2$ | O | 125–126 |
| 1.049 | $CH_3$ | CN | H | $CH_2CH(CH_3)_2$ | O | 130–131 |
| 1.050 | $CH_3$ | CN | H | $CH(CH_3)_2$ | O | 138–139 |
| 1.051 | $C_2H_5$ | CN | H | $CH(CH_3)_2$ | S | 165 |
| 1.052 | $CH(CH_3)_2$ | CN | H | $CH=C(CH_3)_2$ | S | 197–198 |
| 1.053 | $C_6H_5$ | $CONH_2$ | H | $CH_3$ | S | 217–218 |
| 1.054 | $CH(CH_3)_2$ | $CONH_2$ | H | $C_3H_7$ | S | 152–153 |
| 1.055 | $CH(CH_3)_2$ | $CONH_2$ | H | $OC_2H_5$ | S | 145–148 |
| 1.056 | $CH(CH_3)_2$ | $CONH_2$ | H | $C_3H_5$ | S | 204–206 |
| 1.057 | $CH(CH_3)_2$ | $CONH_2$ | H | $CH_2CH_2CH_2Cl$ | S | 127–128 |
| 1.058 | $CH(CH_3)_2$ | $CONH_2$ | H | $CH(CH_3)C_2H_5$ | S | 130–131 |
| 1.059 | $CH(CH_3)_2$ | $CONH_2$ | H | $CH_2CH(CH_3)_2$ | S | 155–157 |
| 1.060 | $CH_3$ | $CONH_2$ | H | $CH_3$ | S | 206–209 |
| 1.061 | $CH_3$ | $CONH_2$ | H | $CH_2CH(CH_3)_2$ | S | 155–158 |
| 1.062 | $CH_3$ | $CONH_2$ | H | $CH(CH_3)C_2H_5$ | S | 135 |
| 1.063 | $CH_3$ | $CONH_2$ | H | $C_3H_7$ | S | 154–156 |
| 1.064 | $C_2H_5$ | $CONH_2$ | H | $C_6H_5$ | S | 228–232 |
| 1.065 | $C_2H_5$ | $CONH_2$ | H | $OC_2H_5$ | S | 153 |
| 1.066 | $C_2H_5$ | $CONH_2$ | H | $C_3H_5$ | S | 176–179 |
| 1.067 | $C_2H_5$ | $CONH_2$ | H | $C(CH_3)_3$ | S | 186 |
| 1.068 | $C_2H_5$ | $CONH_2$ | H | $CH(CH_3)C_2H_5$ | S | 120–122 |
| 1.069 | $C_2H_5$ | $CONH_2$ | H | $CH_2CH(CH_3)_2$ | S | 103 |
| 1.070 | $C_2H_5$ | $CONH_2$ | H | $CH_2CH_2CH_2Cl$ | S | 97 |

-continued

Active ingredients table

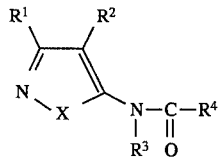

| No. | $R^1$ | $R^2$ | $R^3$ | $R^4$ | X | phys. data mp./$^1$H-NMR [°C.]/δ[ppm] |
|---|---|---|---|---|---|---|
| 1.071 | $C_2H_5$ | $CONH_2$ | H | $C_3H_7$ | S | 125–127 |
| 1.072 | $CH_3$ | $CONH_2$ | H | $C(CH_3)_3$ | S | 190–194 |
| 1.073 | $CH(CH_3)_2$ | $CONH_2$ | H | $CH_3$ | S | 220–221 |
| 1.074 | $CH(CH_3)_2$ | $CONH_2$ | H | $4\text{-}Cl\text{-}C_6H_4$ | S | 221–224 |
| 1.075 | $CH(CH_3)_2$ | $CONH_2$ | H | $3\text{-}Cl\text{-}C_6H_4$ | S | 188–189 |
| 1.076 | $CH(CH_3)_2$ | $CONH_2$ | H | $C_2H_5$ | S | 144–146 |
| 1.077 | $CH(CH_3)_2$ | $CONH_2$ | H | $3\text{-}CH_3\text{-}C_6H_4$ | S | 190–192 |
| 1.078 | $CH(CH_3)_2$ | $CONE2$ | H | $CH(CH_3)_2$ | S | 181 |
| 1.079 | $CH(CH_3)_2$ | $CONH_2$ | H | $C(CH_3)_3$ | S | 162 |
| 1.080 | $CH(CH_3)_2$ | $CONH_2$ | H | $C_6H_{11}$ | S | 188–189 |
| 1.081 | $C_2H_5$ | $CONH_2$ | H | $CH(CH_3)_2$ | S | 144–145 |
| 1.082 | $CH_3$ | $CONH_2$ | H | $C_3H_5$ | S | 229–231 |
| 1.083 | $CH(CH_3)_2$ | $CSNH_2$ | H | $CH_3$ | S | 223–224 |
| 1.084 | $CH(CH_3)_2$ | $CSNH_2$ | H | $C_2H_5$ | S | 168–169 |
| 1.085 | $(CH_2)_2OCH_3$ | $CSNH_2$ | H | $C_2H_5$ | S | 113–114 |
| 1.086 | $CH(CH_3)_2$ | $CSNH_2$ | H | $CH(CH_3)_2$ | S | 157–158 |
| 1.087 | $(CH_2)_2OCH_3$ | $CSNH_2$ | H | $C(CH_3)_3$ | S | 144–145 |
| 1.088 | $CH(CH_3)_3$ | $CSNH_2$ | H | $C(CH_3)_3$ | S | 175–176 |
| 1.089 | $C_3H_7$ | $CSNH_2$ | H | $CH(CH_3)_2$ | S | 181–182 |
| 1.090 | $C_3H_7$ | $CSNH_2$ | H | $C(CH_3)_3$ | S | 186–187 |
| 1.091 | $CH(CH_3)_2$ | $CSNH_2$ | H | $C_3H_7$ | S | 146–147 |
| 1.092 | $CH(CH_3)_2$ | $CSNH_2$ | H | $C_6H_5$ | S | 218–220 |
| 1.093 | $CH(CH_3)_2$ | $CSNH_2$ | H | $OC_2H_5$ | S | 155–158 |
| 1.094 | $CH(CH_3)_2$ | $CSNH_2$ | H | $CH_2CH_2CH_2Cl$ | S | 127–128 |
| 1.095 | $CH(CH_3)_2$ | $CSNH_2$ | H | $CH(CH_3)C_2H_5$ | S | 136–137 |
| 1.096 | $C_2H_5$ | $CSNH_2$ | H | $CH(CH_3)_2C_2H_5$ | S | 144 |
| 1.097 | $C_2H_5$ | $CSNH_2$ | H | $CH_2CH(CH_3)_2$ | S | 181 |
| 1.098 | $C_2H_5$ | $CSNH_2$ | H | $CH_2CH_2CH_2Cl$ | S | 111 |
| 1.099 | $C_2H_5$ | $CSNH_2$ | H | $C_3H_7$ | S | 168 |
| 1.100 | $CH_3$ | $CSNH_2$ | H | $C(CH_3)_3$ | S | 182–185 |
| 1.101 | $C_2H_5$ | $CSNH_2$ | H | $OC_2H_5$ | S | 183–184 |
| 1.102 | $C_2H_5$ | $CSNH_2$ | H | $C(CH_3)_3$ | S | 168 |
| 1.103 | $CH_3$ | $CSNH_2$ | H | $CH(CH_3)C_2H_5$ | S | 164 |
| 1.104 | $CH(CH_3)_2$ | $CSNH_2$ | H | $4\text{-}Cl\text{-}C_6H_4$ | S | 236 |
| 1.105 | $CH(CH_3)_2$ | $CSNH_2$ | H | $3\text{-}CH_3\text{-}C_6H_4$ | S | 199 |
| 1.106 | $CH(CH_3)_2$ | $CSNH_2$ | H | $C_6H_5$ | S | 198–199 |
| 1.107 | $CH_3$ | $CSNH_2$ | H | $CH_2CH(CH_3)_2$ | S | 224–226 |
| 1.108 | $CH_3$ | $CSNH_2$ | H | $C_3H_7$ | S | 187 |
| 1.109 | $C_2H_5$ | $CSNH_2$ | H | $C_3H_5$ | S | 197–198 |
| 1.110 | $CH(CH_3)_2$ | $CSNH_2$ | H | $C_6H_{11}$ | S | 170–171 |
| 1.111 | $CH_3$ | $CSNH_2$ | H | $CH_3$ | S | 222 |
| 1.112 | $CH(CH_3)_2$ | $CN$ | H | $C(CH_3)_3$ | O | 164–165 |
| 1.113 | $CH_3$ | $CN$ | H | $CH(CH_3)C_2H_5$ | O | 128–129 |
| 1.114 | $CH_3$ | $CN$ | H | $C_6H_{11}$ | O | 205–207 |
| 1.115 | $CH_3$ | $CN$ | H | $C_2H_5$ | O | 166–167 |
| 1.116 | $CH_3$ | $CN$ | H | $C_3H_5$ | O | 155–157 |
| 1.117 | $CH_3$ | $CSNH_2$ | H | $CH(CH_3)C_2H_5$ | O | 126–129 |
| 1.118 | $CH_3$ | $CSNH_2$ | H | $CH_2CH(CH_3)_2$ | O | 145–147 |
| 1.119 | $CH(CH_3)_2$ | $CONH_2$ | H | $CH_2CH(CH_3)_2$ | O | 183–186 |
| 1.120 | $CH_2CH_2OCH_3$ | $CN$ | H | $CH(CH_3)C_2H_5$ | S | 88–92 |
| 1.121 | $CH_2CH_2OCH_3$ | $CN$ | H | $CH_2CH(CH_3)_2$ | S | 150–153 |
| 1.122 | $CH_2CH_2OCH_3$ | $CN$ | H | $C(CH_3)_3$ | S | 68–70 |
| 1.123 | $CH_2CH_2OCH_3$ | $CN$ | H | $C_2H_5$ | S | 136–138 |
| 1.124 | $CH_2CH_2OCH_3$ | $CN$ | H | $C_3H_5$ | S | 191–193 |
| 1.125 | $CH_2CH_2OCH_3$ | $CONH_2$ | H | $CH(CH_3)C_2H_5$ | S | 35–40 |
| 1.126 | $CH_2CH_2OCH_3$ | $CONH_2$ | H | $CH_2CH(CH_3)_2$ | S | 93–95 |
| 1.127 | $CH_2CH_2OCH_3$ | $CONH_2$ | H | $C_2H_5$ | S | 114–115 |
| 1.128 | $CH_2CH_2OCH_3$ | $CONH_2$ | H | $C_3H_5$ | S | 166–169 |
| 1.129 | $CH_2CH_2OCH_3$ | $CONH_2$ | H | $C(CH_3)_3$ | S | 88–89 |
| 1.130 | $C_3H_7$ | $CONH_2$ | H | $CH(CH_3)_2$ | S | 155–157 |
| 1.131 | $CH(CH_3)_2$ | $CSNH_2$ | H | $C_3H_5$ | S | 205 |
| 1.132 | $C_2H_5$ | $CSNH_2$ | H | $CH(CH_3)_2$ | S | 178–179 |
| 1.133 | $CH(CH_3)_2$ | $CSNH_2$ | H | $CH_2CH(CH_3)_2$ | S | 110–120 |
| 1.134 | $CH_3$ | $CSNH_2$ | H | $C_3H_5$ | S | 199 |
| 1.135 | $C_2H_5$ | $CN$ | H | $CH_2CH(CH_3)_2$ | O | 153–154 |

-continued

Active ingredients table

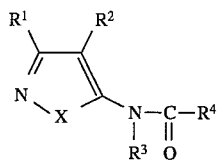

| No. | R¹ | R² | R³ | R⁴ | X | phys. data mp./¹H-NMR [°C.]/δ[ppm] |
|---|---|---|---|---|---|---|
| 1.136 | $C_2H_5$ | CN | H | $C_3H_7$ | O | 153–154 |
| 1.137 | $C_2H_5$ | CN | H | $C(CH_3)_3$ | O | 154–155 |
| 1.138 | $C_2H_5$ | CN | H | $C_2H_5$ | O | 140–141 |
| 1.139 | $C_2H_5$ | CN | H | $C_6H_5$ | O | 165–166 |
| 1.140 | $C_2H_5$ | CN | H | $C_6H_{11}$ | O | 191–193 |
| 1.141 | $C_2H_5$ | CN | H | $CH(CH_3)C_2H_5$ | O | 105–114 |
| 1.142 | $CH(CH_3)_2$ | CN | H | $CH=CH_2$ | S | 210–211 |
| 1.143 | $C_2H_5$ | CN | H | $C_3H_5$ | O | 129–133 |
| 1.144 | $C_2H_5$ | CN | H | $CH(CH_3)_2$ | O | 164–166 |
| 1.145 | $CH(CH_3)C_2H_5$ | CN | H | $C_2H_5$ | O | 110–113 |
| 1.146 | $C_2H_5$ | CN | H | $CH_2CH_2CH_2Cl$ | O | |
| 1.147 | $CH(CH_3)_2$ | CN | H | $CH=CHCH_3$ | S | 208–209 |
| 1.148 | $CH(CH_3)_2$ | CN | H | $C(CH_3)=CH_2$ | S | 123–124 |
| 1.149 | $C_2H_5$ | CN | H | $CH_3$ | S | 200–204 |
| 1.150 | $C(CH_3)_3$ | CN | H | $C_2H_5$ | S | 143–144 |
| 1.151 | $C(CH_3)_3$ | CN | H | $CH(CH_3)_2$ | S | 160–162 |
| 1.152 | $C(CH_3)_3$ | CN | H | $CH(CH_3)C_2H_5$ | S | 134–137 |
| 1.153 | $C(CH_3)_3$ | CN | H | $C(CH_3)_3$ | S | 197–199 |
| 1.154 | $C(CH_3)_3$ | CN | H | $C_3H_5$ | S | 178–179 |
| 1.155 | $C(CH_3)_3$ | CN | H | $CH_3$ | S | 158–159 |
| 1.156 | $CH(CH_3)_2$ | $CONH_2$ | H | $C(CH_3)_2C_3H_7$ | S | 165–166 |
| 1.157 | $CH(CH_3)_2$ | $CONH_2$ | H | $C_4H_7$ | S | 190–191 |
| 1.158 | $CH(CH_3)_2$ | $CONH_2$ | H | $CH_2C(CH_3)_3$ | S | 146–147 |

Use examples:

The herbicidal action of the acylamino-substituted isoxazole or isothiazole derivatives of the formula I on the growth of the test plants was demonstrated by the following greenhouse experiments.

The culture vessels used were plastic flower pots containing loamy sand with about 0.3% of humus as a substrate. The seeds of the test plants were sown separately according to species.

In the preemergence treatment, the active ingredients suspended or emulsified in water were applied directly after sowing, by means of finely distributing nozzles. The vessels were lightly sprinkler-irrigated in order to promote germination and growth and were then covered with transparent plastic covers until the plants had started to grow. This covering ensures uniform germination of the test plants, provided that they have not been adversely affected by the active ingredients.

For the purpose of the postemergence treatment, the test plants were grown to a height of from 4 to 15 cm, depending on the form of growth, before being treated with the active ingredients suspended or emulsified in water. For this purpose, either the test plants were directly sown and grown in the same vessels or they were first grown separately as seedlings and transplanted into the test vessels a few days before the treatment. The application rate for the postemergence treatment was 0.25 kg/ha of active substance.

The plants were kept at 10°–25° C. or 20°–35° C., depending on the species. The experimental period extended over from 2 to 4 weeks. During this time, the plants were tended and their reaction to the individual treatments was evaluated.

Evaluation was based on a scale from 0 to 100. 100 means no germination of the plants or complete destruction of at least the above-ground parts and 0 means no damage or normal course of growth.

The plants used in the greenhouse experiments consisted of the following species:

| Botanical name | Common name |
|---|---|
| *Chenopodium album* | common lambsquarters |
| *Polygonum persicaria* | ladysthumb |

Using 0.25 kg/ha of active substance by the postemergence method, undesirable plants could be very well controlled with examples No. 1.043 and 1.044.

Compared with structurally similar prior art compounds, for example compound A

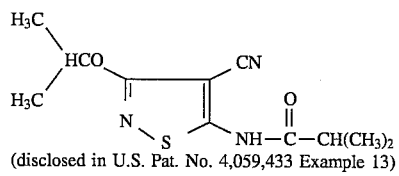

(disclosed in U.S. Pat. No. 4,059,433 Example 13)

or compound B

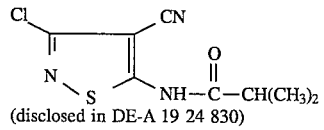

(disclosed in DE-A 19 24 830)

the novel compounds have a better herbicidal action or higher selectivity, as indicated by the results shown in Tables I and II below. The experimental procedure was as described above for the postemergence method.

TABLE I

Herbicidal action of compounds 1.043 and comparative substance A by the postemergence method (greenhouse)

| Compound | Application rate [kg/ha] a.i. | Test plants [damage in %] | | |
|---|---|---|---|---|
| | | ECHCG | ABUTH | IPOSS |
| 1.043 | 1.0 | 100 | 100 | 100 |
| | 0.5 | 100 | 100 | 100 |
| A | 1.0 | 20 | 15 | 40 |
| | 0.5 | 0 | 10 | 25 |

ECHCG = *Echinochloa crus-galli*
ABUTH = *Abutilon theophrasti*
IPOSS = *Ipomoea ssp.*

TABLE II

Herbicidal action and selectivities of the compounds 1.044 and comparative substance B by the postemergence method (greenhouse)

| Compound | Application rate [kg/ha] a.i. | Test plants [damage in %] | | | | |
|---|---|---|---|---|---|---|
| | | Crops | | undesirable plants | | |
| | | TRZAS | ZEAMX | ECHCG | SETVI | ABUTH |
| 1.044 | 1.0 | 0 | 10 | 100 | 100 | 100 |
| | 0.5 | 0 | 10 | 90 | 100 | 100 |
| B | 1.0 | 70 | 85 | 98 | 100 | 100 |
| | 0.5 | 50 | 85 | 98 | 100 | 100 |

TRZAS = *Triticum aestivum* (summer wheat)
ZEAMX = *Zea mays* (corn)
ECHCG = *Echinochloa crus-galli*
SETVI = *Setaria viridis*
ABUTH = *Abutilon theophrasti*

We claim:
1. An acylamino-substituted isothiazole derivative the formula I

$$\underset{R^3\ \ O}{\overset{R^1\quad R^2}{\underset{\diagdown}{\underset{X}{\overset{\diagup\diagup}{N}}}\underset{}{=}\underset{}{}\underset{}{N}-\overset{}{\underset{|}{C}}-R^4}}$$ I where X is sulfur, $R^1$ is $C_1-C_6$-alkyl which is substituted by from one to three halogen atoms or one cyano radical or up to two of the following radicals: $C_1-C_4$-alkoxy, $C_1-C_4$-haloalkoxy, $C_1-C_4$-alkylthio, $C_1-C_4$-haloalkylthio, $C_3-C_6$-cycloalkyl, which in turn may be substituted by from one to three halogen or alkyl radicals, or phenyl which may furthermore carry from one to three of the following radicals: cyano, nitro, halogen, $C_1-C_6$-alkyl, $C_1-C_1$-haloalkyl, $C_1-C_1$-alkoxy, $C_1-C_1$-haloalkoxy, $C_1-C_6$alkylthio or $C_1-C_6$-haloalkylthio, $C_2-C_6$-alkenyl, whose double bond may be epoxidized, $C_2-C_6$-alkynyl, where both groups may be monosubstituted to trisubstituted by halogen or $C_1-C_1$-alkoxy or monosubstituted by cyclopropyl or phenyl, where the phenyl, where radical may additionally carry from one to three of the following substituents: halogen, cyano, nitro, $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio;

$R^2$ is CN, $CONH_2$, $CSNH_2$ or $C_1-C_2$-haloalkyl;

$R^3$ is hydrogen;

$C_1-C_6$-alkyl which may carry from one to three of the following substituents: hydroxyl, halogen, $C_1-C_4$-alkoxy or $C_1-C_4$-alkylthio;

$C_3-C_8$-cycloalkyl which may be monosubstituted to trisubstituted by halogen, $C_1-C_4$-alkyl or $C_1-C_4$-haloalkyl;

$R^4$ is $C_1-C_1$-alkoxy;

$C_1-C_6$-alkyl which may carry from one to three of the following radicals: halogen, cyano, $C_1-C_4$-alkoxy, $C_1-C_4$-haloalkoxy, $C_1$ -$C_4$-alkylthio, $C_1-C_1$-haloalkylthio, $C_3-C_8$-cycloalkyl or phenyl, where the phenyl ring in turn may carry from one to three of the following radicals: halogen, cyano, nitro, $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio;

$C_3-C_8$-cycloalkenyl which may be monosubstituted to trisubstituted by halogen or by $C_1-C_4$-alkyl;

$C_3-C_8$-cycloalkyl which may carry from one to three of the following radicals: halogen, nitro, cyano, $C_1-C_6$-alkyl, $C_1-C_6$-haloalkyl, $C_1-C_4$-alkoxy or $C_1-C_4$-haloalkoxy; $C_3-C_6$-alkenyl or $C_3-C_6$-alkynyl, each of which may be monosubstituted to trisubstituted by halogen or monosubstituted by phenyl, where the phenyl radical in turn may carry from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano or nitro; a 5-membered or 6-membered heterocyclic saturated or aromatic radical having one or two hetero atoms selected from the group consisting of oxygen, sulfur and nitrogen, which may be monosubstituted to trisubstituted by $C_1-C_4$-alkyl or by halogen; phenyl which may furthermore carry from one to three of the following radicals: cyano, nitro, halogen, $C_1-C_6$-alkyl, $C_1-C_6$haloalkyl, $C_1-C_6$-alkoxy, $C_1-C_6$-haloalkoxy, $C_1-C_6$-alkylthio or $C_1$ -$C_6$-haloalkylthio;

and agriculturally useful salts of the isoxazole or isothiazole derivative I, with the exception of:

3-methyl-4-cyano-5-benzoylaminoisothiazole, 3-methyl-4-carboxamido-5-acetylaminoisothiazole,
3-methyl-4-carboxamido-5-(4-chlorobenzoyl)-aminoisothiazole,
3-methyl-4-carboxamido-5-(2-chlorobenzoyl)-aminoisothiazole and
3-methyl-4-carboxamido-5-benzoylaminoisothiazole
and with the proviso that when $R^1$ is ethyl or methyl, $R^4$ is methyl and $R^2$ is carboxamide, the ethyl or methyl must be substituted.

2. An isothiazole derivative of the formula I as defined in claim 1, where $R^2$, $R^3$ and $R^4$ have the meanings stated in claim 1 and $R^1$ is $C_2$–$C_6$-alkyl or methyl which is substituted by from one to three halogen atoms or one cyano radical or up to two of the following radicals: $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, which in turn may be substituted by from one to three halogen or alkyl radicals, or phenyl which may furthermore carry from one to three of the following radicals: cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio or $C_1$–$C_6$-haloalkylthio.

3. An isothiazole derivative of the formula I as defined in claim 1, where $R^1$, $R^2$ and $R^3$ have the meanings stated in claim 1 and $R^4$ is a 5-membered or 6-membered saturated or aromatic heterocyclic radical selected from the group consisting of 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl and 4-pyridyl, where this radical may carry from one to three of the following substituents: $C_1$–$C_4$-alkyl or halogen.

4. An isothiazole derivative of the formula I as defined in claim 1

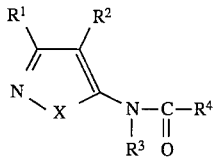

where

X is oxygen or sulfur;

$R^1$ is $C_2$–$C_6$-alkyl, $C_2$–$C_6$-alkenyl, $C_2$–$C_6$-alkynyl, $C_3$–$C_8$-cycloalkyl or $C_3$–$C_6$-cycloalkenyl, where each of these groups may be substituted as defined in claim 1;

$R^2$ is CN, $CONH_2$ or $CSNH_2$;

$R^3$ is hydrogen or $C_1$–$C_6$-alkyl and $R^4$ is $C_1$–$C_4$-alkoxy, $C_1$–$C_6$-alkyl or $C_3$–$C_8$-cycloalkyl, where the alkyl and cycloalkyl radicals may be substituted as defined in claim 1.

5. A herbicidal composition containing a herbicidally effective amount of an acylamino-substituted isoxazole or isothiazole derivative of the formula I as defined in claim 1 and inert additives.

6. A method for controlling undesirable plant growth, wherein the plants or their habitat are treated with a herbicidally effective amount of an acylamino-substituted isothiazole derivative of the formula I as claimed in claim 1.

7. An acylamino-substituted isothiazole derivative of the formula I as defined in claim 1, wherein $R^1$ is isopropyl, $R^2$ is CN, $R^3$ is H, $R^4$ is isopropyl, and X is S.

8. A method of controlling undesirable plant growth, wherein the plants or their habitat are treated with a herbicidally effective amount of an acylamino-substituted isothiazole derivative of the formula I as defined in claim 7.

9. An acylamino-substituted isothiazole derivative of the formula I as defined in claim 1, wherein $R^1$ is ethyl, $R^2$ is —$CONH_2$, $R^3$ is H, $R^4$ is isopropyl, and X is S.

10. A method of controlling undesirable plant growth, wherein the plants or their habitat are treated with a herbicidally effective amount of an acylamino-substituted isothiazole derivative of the formula I as defined in claim 9.

* * * * *

UNITED STATES PATENT AND TRADEMARK OFFICE
CERTIFICATE OF CORRECTION

PATENT NO.: 5,538,939  Page 1 of 2

DATED: July 23 1996

INVENTOR(S): MUENSTER et al.

It is certified that error appears in the above-identified patent and that said Letters Patent is hereby corrected as shown below:

On the title page, item [57], in the last line of the Abstract, delete "useful as herbicides." and substitute the following:

--with the exception of 3-methyl-4-cyano-5-fur-2-ylcarbonylaminoisoxazole,
3-ethyl-4-cyano-5-fur-2-ylcarbonylaminoisoxazole,
3-methyl-4-cyano-5-benzoylaminoisothiazole,
3-methyl-4-carboxamido-5-acetylaminoisothiazole,
3-methyl-4-carboxamido-5-(4-chlorobenzoyl)-aminoisothiazole,
3-methyl-4-carboxamido-5-(2-chlorobenzoyl)-aminoisothiazole, agent containing the compounds I and their use as herbicides.--

UNITED STATES PATENT AND TRADEMARK OFFICE
CERTIFICATE OF CORRECTION

PATENT NO.: 5,538,939

DATED: July 23 1996

INVENTOR(S): MUENSTER et al.

It is certified that error appears in the above-identified patent and that said Letters Patent is hereby corrected as shown below:

Column 21, claim 1, line 61, "$C_1$-$C_1$-haloalkyl, $C_1$-$C_1$-alkoxy, $C_1$-$C_1$-haloalkoxy" should read --$C_1$-$C_6$-haloalkyl, $C_1$-$C_6$-alkoxy, $C_1$-$C_6$-haloalkoxy--;

line 65, "$C_1$-$C_1$-alkoxy" should read --$C_1$-$C_6$-alkoxy--;

lines 66-67, delete ", where".

Column 22, claim 1, line 14, "$C_1$-$C_1$-alkoxy" should read --$C_1$-$C_4$-alkoxy;

line 17, "$C_1$-$C_1$-haloalkylthio" should read --$C_1$-$C_4$-haloalkylthio--.

Signed and Sealed this

Fifteenth Day of October, 1996

Attest:

BRUCE LEHMAN

Attesting Officer

Commissioner of Patents and Trademarks